US009022992B2

(12) United States Patent
Helmer et al.

(10) Patent No.: US 9,022,992 B2
(45) Date of Patent: May 5, 2015

(54) DRUG DELIVERY DEVICE

(75) Inventors: Michael Helmer, Frankfurt am Main (DE); Steffen Raab, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 128 days.

(21) Appl. No.: 13/512,180

(22) PCT Filed: Dec. 2, 2010

(86) PCT No.: PCT/EP2010/068706
§ 371 (c)(1),
(2), (4) Date: Oct. 23, 2012

(87) PCT Pub. No.: WO2011/067320
PCT Pub. Date: Jun. 9, 2011

(65) Prior Publication Data
US 2013/0041325 A1 Feb. 14, 2013

(30) Foreign Application Priority Data

Dec. 3, 2009 (EP) .................................... 09177940

(51) Int. Cl.
*A61M 5/00* (2006.01)
*A61M 5/315* (2006.01)
(Continued)

(52) U.S. Cl.
CPC ......... *A61M 5/31555* (2013.01); *A61M 5/3146* (2013.01); *A61M 5/24* (2013.01); *A61M 5/3156* (2013.01); *A61M 5/3158* (2013.01); *A61M 5/31593* (2013.01); *A61M 2005/31506* (2013.01)

(58) Field of Classification Search
CPC ..................... A61M 5/31533; A61M 5/31536; A61M 5/31543; A61M 5/31545; A61M 5/31548; A61M 5/31551; A61M 5/31563; A61M 5/31593; A61M 5/31595; A61M 5/315; A61M 5/24; A61M 5/3146; A61M 5/3156; A61M 5/3158; A61M 2005/31506; F16F 1/14; F16F 1/025; F16F 1/027; F16F 1/324; F16F 1/48; F16F 1/428; F16H 55/28; F16H 2057/126; F16H 2057/127; B24B 47/00
USPC ............. 604/187, 207, 208, 209, 224; 74/409
See application file for complete search history.

(56) References Cited

U.S. PATENT DOCUMENTS 2,695,023 A 11/1954 Brown
3,121,516 A 2/1964 Dewees et al.
(Continued)

FOREIGN PATENT DOCUMENTS

GB 2142245 1/1985
JP H07-509170 10/1995
(Continued)

OTHER PUBLICATIONS

European Search Report for European App. No. 09177940.5, completed Apr. 29, 2010.
(Continued)

*Primary Examiner* — Bhisma Mehta
*Assistant Examiner* — Nicholas Meghri
(74) *Attorney, Agent, or Firm* — McDonnell Boehnen Hulbert & Berghoff LLP

(57) ABSTRACT

A drug delivery device comprises a housing and a piston rod arranged in the housing. The piston rod is adapted to be moved along an axial direction to dispense a fluid. A drive member arranged in the housing is operatively coupled to the piston rod and adapted to set up a dose of fluid for dispense in response to a first movement. The drive member is also adapted to move the piston rod to dispense the dose in response to a second movement. The drug delivery device also comprises a pre-dispensing drive member operatively coupled to the drive member and the housing and adapted to move at least the drive member by a pre-dispensing distance between its first and second movement.

16 Claims, 4 Drawing Sheets

(51) Int. Cl.
*A61M 5/31* (2006.01)
*A61M 5/24* (2006.01)

(56) References Cited

U.S. PATENT DOCUMENTS

| | | | | |
|---|---|---|---|---|
| 4,022,207 A | | 5/1977 | Citrin | |
| 5,342,304 A | * | 8/1994 | Tacklind et al. | 604/99.01 |
| 5,496,293 A | | 3/1996 | Huggenberger | |
| 5,599,314 A | * | 2/1997 | Neill | 604/207 |
| 6,228,067 B1 | * | 5/2001 | Gabriel | 604/211 |
| 2006/0229570 A1 | | 10/2006 | Lovell et al. | |
| 2008/0147005 A1 | * | 6/2008 | Moller et al. | 604/134 |

FOREIGN PATENT DOCUMENTS

| | | |
|---|---|---|
| WO | 94/15120 | 7/1994 |
| WO | 94/26331 | 11/1994 |
| WO | 96/26754 | 9/1996 |

OTHER PUBLICATIONS

International Search Report for International App. No. PCT/EP2010/068706, completed Apr. 1, 2011.
English translation of the Chinese Second Office Action for CN App. No. 2010800631013, dated Jul. 26, 2013.
Japanese Office Action for JP App. No. 2012-541499, mailed Aug. 12, 2014.

* cited by examiner

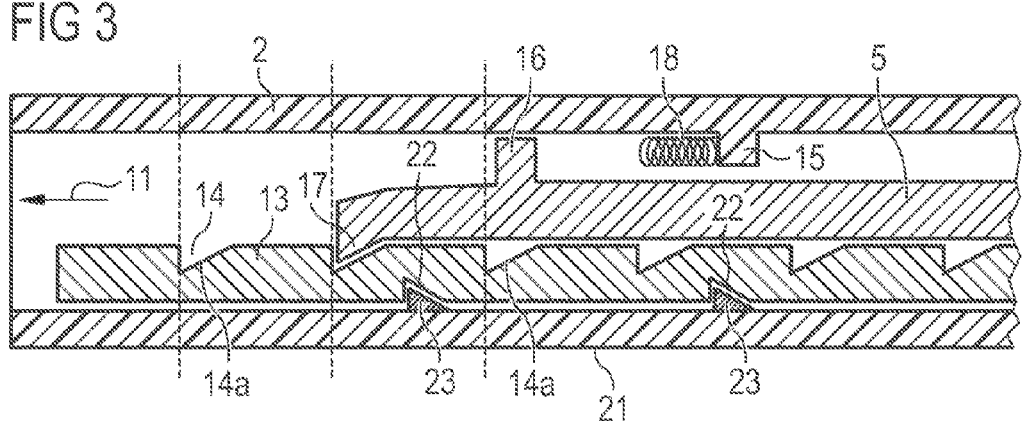
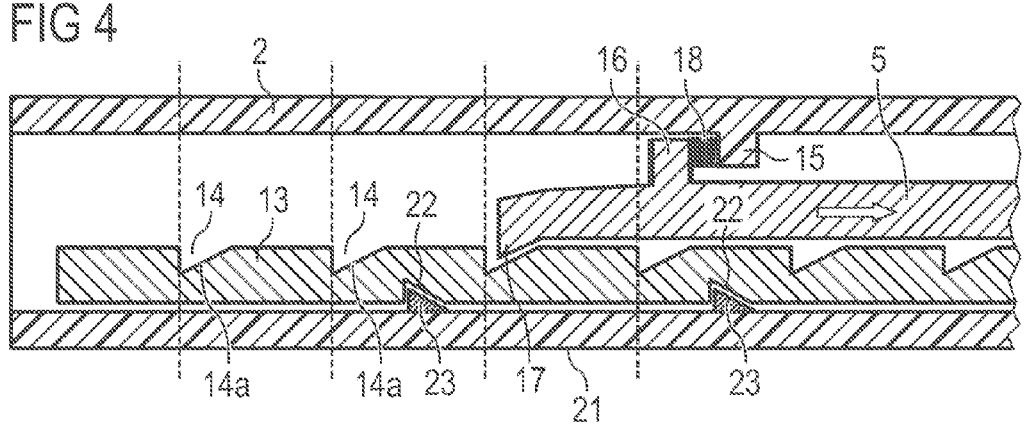
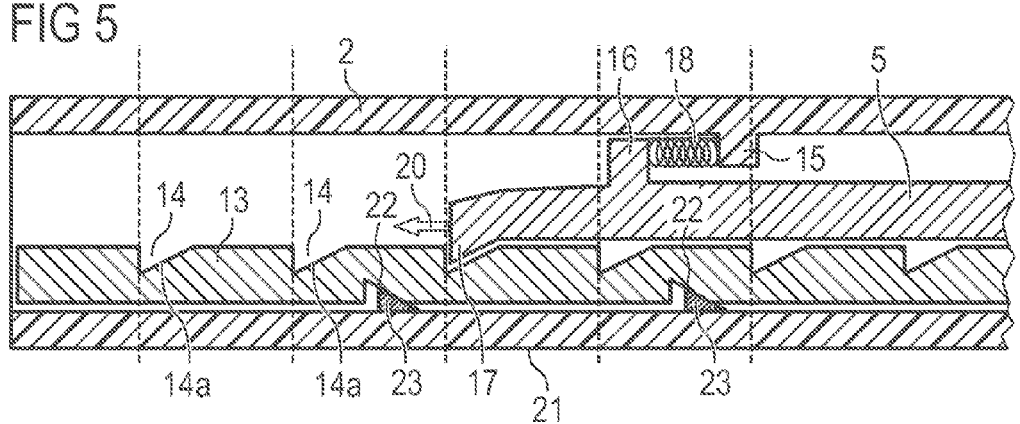

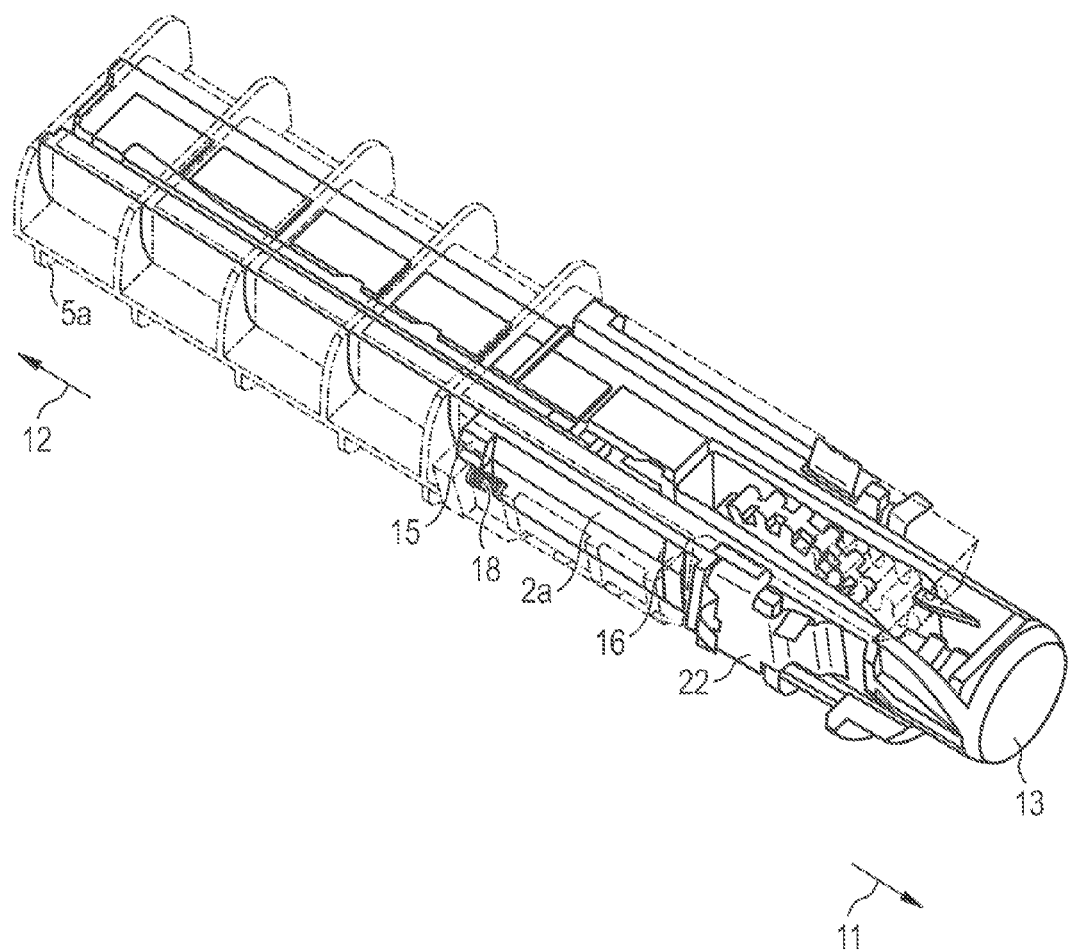

DRUG DELIVERY DEVICE

CROSS REFERENCE TO RELATED APPLICATIONS

The present application is a U.S. National Phase Application pursuant to 35 U.S.C. §371 of International Application No. PCT/EP2010/068706 filed Dec. 2, 2010, which claims priority to European Patent Application No. 09177940.5 filed on Dec. 3, 2009. The entire disclosure contents of these applications are herewith incorporated by reference into the present application.

FIELD OF THE INVENTION

The present invention is related to a drug delivery device, in particular to a pen-type injector, wherein a number of pre-set doses of a medicinal product can be administered.

BACKGROUND

Drug delivery devices have application, where persons without formal medical training need to administer an accurate and predefined dose of a medicinal product, such as heparin or insulin. In addition, the medicinal product may be administered on an irregular basis over a short-term or a long-term period.

User operated drug delivery devices are well-known within the medical field.

WO 96/26754 A2 shows a mechanism for accurate dispensing of pre-set quantities of medicinal products from a drug delivery device wherein a rotatable plunger has a number of parallel racks on its internal surface each of which comes into engagement with the first tooth wheel as a piston rod rotates when a dose is set. The device has a second tooth wheel that rotates with the first tooth wheel thus driving a thrust rod into the drug delivery device when the selected dose is delivered.

A user, for instance a patient, may inject a fluid into its body by selecting the pre-set dose. For that purpose, the user moves the button of the drug delivery device by a first movement to pre-set the dose to be administered. With a second movement of the dose button, the fluid is dispensed and may be injected into the patient's body. The procedure can be repeated upon the patient's discretion.

Depending on the medicinal product to be administered, a single dose must be very accurate and the amount of fluid shall not differ between different doses. As the mechanical parts of the drug delivery device comprise some tolerances in between, the device is primed before the first usage. During the priming procedure, all mechanical parts of the drive mechanism of the drug delivery device are initialized and any backlash as well as tolerances between different mechanical parts is reduced.

However, a backlash may occur and tolerances between the different parts of the drive mechanism may increase during the dispensing of several doses. Accordingly, the accuracy of amounts of doses to be dispensed will decrease again. In summary, there is still a need for drug delivery devices with improved dose accuracy during usage.

SUMMARY

For this object, a drug delivery device may comprise a housing and a piston rod arranged in the housing. The piston rod is adapted to be moved along an axial direction to dispense a fluid. A drive member, also arranged in the housing is operatively coupled to the piston rod. The drive member is adapted to set up a dose of fluid for dispense in response to a first movement and further adapted to move the piston rod along the axial direction to dispense a dose in response to a second movement. The drug delivery device further comprises a pre-dispensing spring member operatively coupled to the drive member and the housing. The spring member is adapted to move at least the drive member by a pre-dispensing distance between the first and second movement.

Accordingly, in an embodiment at least the drive member is moved a pre-dispensing distance after setting up a dose and before actual dispensing the previously set up dose. Such additional movement by a pre-dispensing distance will reduce any backlashes or tolerances which may occur between dispensing several doses of fluid. Accordingly, the amount of fluid dispensed during each second movement will be substantially constant and not vary during different dispense procedures.

The first and second movement of the drive member may be initiated by a moveable dose button, said dose button operatively connected to the drive member.

In this respect, the first movement of the drive member or the first movement of the dose button indicates a movement for selecting a dose to be dispensed. Accordingly, the second movement of the drive member and the dose button respectively indicates a movement of a drive member resulting in dispensation of the previously set up dose of fluid.

If a user moves the dose button in a specific direction, the dose button will operatively act on the drive member resulting in the first movement for setting up the dose of fluid to be dispensed. If the user subsequently moves the button in a second direction the button will act on the drive member resulting in a second movement of the drive member thereby dispensing the dose. Preferably at least one of the directions the dose button is moved may correspond to the first or second direction. For instance the dose button is moved in the first direction for setting up a dose and/or the second direction for acting upon the drive member to dispense the fluid.

In an embodiment, the drive member is operatively coupled to the piston rod and to the dose button to set up a dose of the fluid for dispense in response to a first movement of the dose button and to move the piston rod along the distal direction to dispense the set up dose in response to a second movement of the dose button. Between the first and second movement of the dose button, the pre-dispensing spring member moves at least the drive member a pre-dispensing distance.

In an embodiment, the pre-dispensing spring member may be pre-loaded or pre-tensioned during the first movement of the drive member or the dose button. After the first movement the pre-dispensing spring member is at least partly released and unloaded, respectively, to move at least the drive member and piston rod, respectively by a pre-dispensing distance. By the pre-dispensing distance movement of at least the drive member, any tolerance or backlash which might be introduced during dispensation is reduced. Particularly, during movement of the pre-dispensing distance, the piston rod gets in direct contact with a bung or piston arranged in the cartridge of the drug delivery device.

In another embodiment, the pre-dispensing spring member may exert a force upon the drive member. Said force may cause the movement by a pre-dispensing distance. In any case the force reduces tolerances and backlashes between different parts of the drive member as well as between the drive member and the piston.

In an embodiment of the present invention the pre-dispensing spring member may comprise a first strip portion and a second strip portion, wherein the second strip portion is connected slightly bent to the first strip portion. Accordingly, the pre-dispensing spring member may comprise a V-shaped like form. Alternatively, the pre-dispensing spring member may comprise a bended strip.

In another aspect of the present invention, the pre-dispensing spring member may comprise a torsional stress or strain at least after the first movement of the dose button. In this embodiment, the spring member may be loaded by stressing the spring member torsionally.

In an embodiment, the pre-dispensing spring member may be adapted to exert a reverse-directed force upon the drive member after the first movement. In other words, the spring member may exert a force, which is directed in the opposite direction the drive member was moved during the first movement. Accordingly, during the first movement of the drive member to select the respective dose, the pre-dispensing spring member may generate a force which is parallel to the first movement of the drive member but points into the opposite direction. When a user releases the dose button after selecting the respective dose, the force by the pre-dispensing spring member acts upon the drive member to move the drive member by the pre-dispensing distance in the opposite direction, for instance into the direction of the second movement. Such movement by a pre-dispensing distance will prevent any backlash or tolerances between the different parts of the drive member as well as any tolerance between the piston and the piston rod or the piston rod and the drive member.

In another embodiment, the housing may comprise a stop element to prevent further motion of the drive member during movement of the dose button. The pre-dispensing spring member may be attached to said stop element. As a result, the pre-dispensing spring member will be stressed during the first movement of the drive member and at least partially relieved after the first movement has ended and before the second movement is started. During second movement the pre-dispensing spring member will be relieved completely.

In another embodiment the housing comprises a stop element to prevent further motion of the drive member during movement, wherein the pre-dispensing spring member is attached to the drive member. In any case, during the first movement of the drive member the pre-dispensing spring member is stressed and at least partly relieved after the first movement is finished and before the second movement.

In another embodiment, the pre-dispensing spring member is attached to the housing and the dose button. It is adapted to exert a reverse-directed force upon the dose button in response to the first movement of the dose button.

In another aspect, a drug delivery device further comprises a cartridge holder for holding a cartridge having the fluid and a piston which is arranged between the piston rod and the cartridge. An adhesion force between the piston and the cartridge holder or between the piston and the housing may be greater than a force exerted by the stressed pre-dispensing spring member during the first and second movement of the drive member. In other words, the adhesion force between a piston and the cartridge holder or between the piston and the housing is greater than a force caused by a pre-dispensing spring member. This will prevent the piston to be moved during movement of the drive member after the dose to be dispensed is selected and before actually dispensing the selected dose.

For selecting a dose to be dispensed, the dose button may be adapted to be moved in an axial distal direction. Alternatively, the dose button may be adapted to be rotated to select as a dose of a fluid to be dispensed.

In another embodiment the pre-dispensing spring member comprises a lift in the range of less than 10% and preferably less than 5% of a movement distance of the drive member during dispense of the fluid or the second movement. Accordingly, any pre-dispensing distance caused by the pre-dispensing spring member is less than 10% of the movement of the drive member during its second movement to dispense the selected dose of a fluid.

Other features will become apparent from the following detailed description together with the accompanying drawings in which,

BRIEF DESCRIPTION OF THE FIGURES

FIG. 3 illustrates an embodiment of the present invention in more detail, FIG. 4 shows the embodiment of FIG. 3 during selection of a dose, FIG. 5 shows the embodiment of FIG. 3 before actually dispensing the selected dose, FIG. 7 illustrates the drive member of the embodiment according to FIG. 6.

It should be noted that the description of the drug delivery device as shown in the following figures is merely illustrated. Portions or parts of the drug delivery device are illustrated in large with respect to other parts. However, dimensions of portions and parts of the drug delivery device are for illustrational purposes only and do not represent real dimensions or ratios. Similar parts may comprise the same references.

DETAILED DESCRIPTION

Figure 1:
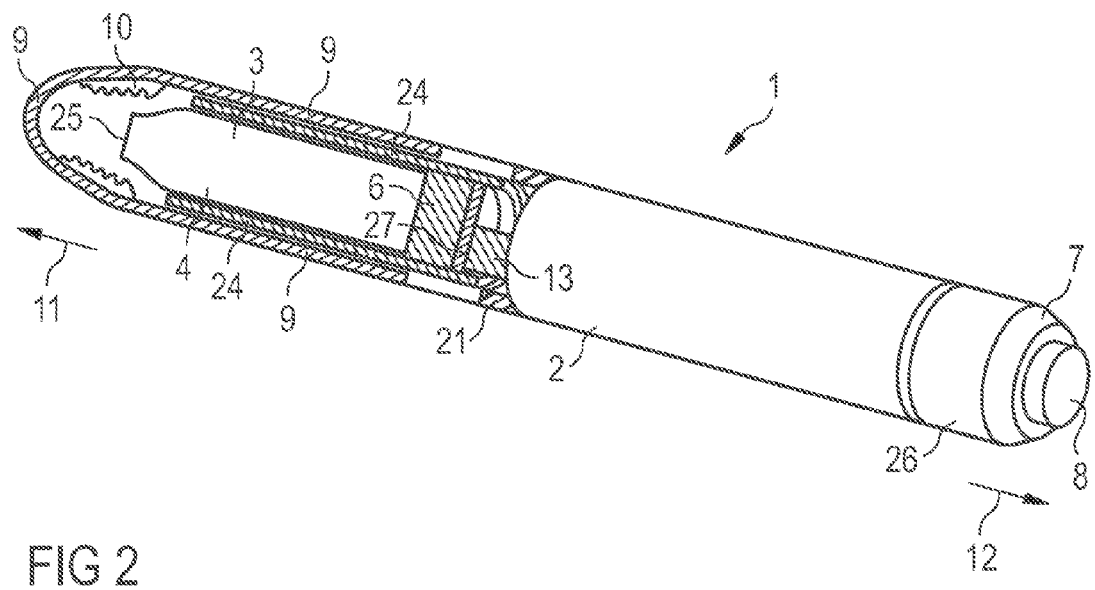
FIG. 1 shows an embodiment of a drug delivery device according to the present invention.

The drug delivery device according to FIG. 1 is configured to deliver a plurality of fixed doses of a drug. The drug delivery device 1 is a pen-type device, preferably a pen-type injector. It comprises a housing 2 and a cap 9 which is connected to the housing to secure a cartridge holder 27. A cartridge 3 is arranged in cartridge holder 27. The cap 9 also comprises engaging means 10 arranged close to an outlet 25 of cartridge 3.

Cap 9 and cartridge holder 24 is arranged at a distal end 11 of drug delivery device 1, while dose button 8, grip surface 26 and dose member 7 are arranged at the proximal end 12 of the drug delivery device. Dose button 8 is an operative connection with a drive member 5 (not shown herein) arranged within the housing 2, which drives piston rod 13 on guide sleeve 21 towards a distal end 11 of the drug delivery device. Piston rod 13 is coupled to piston 6 which is arranged within cartridge 3 to dispense drug fluid 4 within the cartridge.

For dispensing a dose of fluid 4 in the cartridge, a user moves button 8 towards proximal direction 12 to select the dose. The selection will be shown in the next embodiments in figures in greater detail.

For dispensing the preselected dose of fluid the user pushes the button 8 towards the distal end 11, whereby dose button 8 acts upon the drive member and the piston rod 13 to move piston rod 13 by a pre-specified distance towards distal end 11. Such movement will result in dispensing the fluid.

Figure 2:
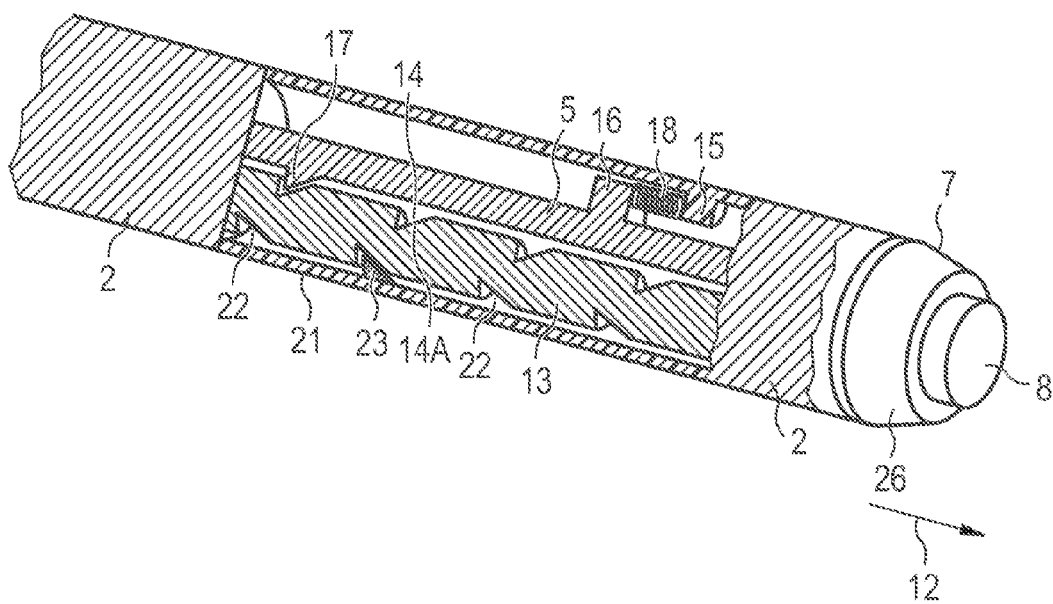
FIG. 2 shows a portion of the drug delivery device according to the present invention.

FIG. 2 shows drive member 5 arranged in housing 2 of drug delivery device 1 in greater detail. The drive member comprises moving rack 5 operatively connected to button 8, said moving rack having displacement members 17. Displacement member 17 is adapted to engage with respective tooth portions 14 arranged on a piston rod 13. By engaging the displacement member 17 with teeth 14a of piston rod 13, the piston rod can be moved towards the distal direction when pushing button 8 in the respective distal direction. As it can be seen, teeth 14a are arranged on the piston rod in equal distances corresponding to fixed selected doses fluids. Alternatively the teeth 14a may comprise different distances between each other.

In addition, guiding sleeve 21 comprises guide stop members 23, which engage respective piston rod stop recesses 22 arranged on piston rod 13. The guiding stop member will prevent the movement of the piston rod towards proximal end 12 during dose selection by moving button 8 and first drive member 5 along proximal direction.

To reduce tolerances and backlashes between selecting a dose and dispensing the preselected dose of fluid, drive member 5 comprises a drive pre-dispensing member stop element 16, which is in operative connection with stop element 15 connected to housing 2. Between stop element 15 and stop element 16 of drive member 5 the pre-dispensing spring element 18 is arranged.

During first movement of button 8 and drive member 5 along the proximal direction 12, spring member 18 is preloaded. When the user releases button 8, pre-dispensing member 18 exerts a force upon stop element 16 and drive member 5 thereby moving drive member 5 by a pre-dispensing distance. This movement of the pre-dispensing distance will achieve a direct contact of displacement member 17 into tooth portion 14 of teeth 14a of piston rod 13 as well as move piston rod 13 until the rod is in direct contact with other piston. Accordingly, the stress relief of spring member 18 will reduce any tolerances between the different mechanical parts of drive member 5, piston rod 13 and the piston such that all parts and portions are in direct contact. Consequently, a user pushing the button 8 into distal direction will now directly dispense the correct amount of fluid without inaccuracy due to variations tolerances and backlashes.

FIG. 3 shows a more detailed view of an embodiment according to the present invention.

In this embodiment, the drug delivery device is in an operating state prior to selecting a dose. The drug delivery device comprises a housing 2 with stop member 15 arranged on the inner sidewall of the housing and facing drive member 5. The drive member 5 comprises stop element 16 facing the inner sidewall of the housing and arranged between the stop end 15 and distal end 11 of drug delivery device 1.

The drive member 5 also comprises displacement member 17 which is adapted to engage teeth 14a being arranged on piston rod 13. As indicated by the dotted lines, tooth portion 14 arranged on piston rod 13 comprise equal distance to each other, corresponding to a fixed preselected dose of fluid. Further, piston rod 13 comprises piston rod stop members 22 which are operatively engaging respective guide stop members 23, said guide stop members 23 being part of guiding sleeve 21. For dispensing a fluid, piston rod 13 moves towards the distal end of drug delivery device 1 thereby pushing bung 6 in the same direction. Such movement is achieved using displacement member 17, which engage tooth portion 14 of teeth 14a. When drive member 4 is moved towards distal end 11, the engaged displacement member 17 pushes piston rod 13 towards the same direction.

FIG. 4 illustrates the status of the drug delivery device during selection of a dose. For that purpose, a dose button (not shown herein), which is operatively connected with drive member 5 is moved along proximal direction thereby causing a proximal directed movement of a drive member 5. Stop element 16 of drive member 5 comes in contact with pre-dispensing spring member 18 during movement into proximal direction 19. Pre-dispensing spring member 18 is thereby loaded until the displacement member 17 snaps into one of the teeth 14a of piston rod 13. The pre-dispensing spring member 18 will remain loaded until the user releases button 8 (not shown herein) thereby also releasing drive member 5, which is operatively connected with button 8. The stress on pre-dispensing spring member 18 generates a force directed in opposite direction of the proximal movement of drive member 5. In other words the stress on pre-dispensing spring member 18 is directed in direction towards distal end 11.

If the distance between the teeth 14a of a pair of adjacent teeth varies along the piston rod 13 (not explicitly shown), the pre-dispensing movement of the drive member 5 may be adjusted or restricted to specific actuations of the button/drive member. For example, if two teeth are spaced at a distance which is less than the distance the drive member 5 has to be moved proximally for pre-loading the spring member 18, there will be no spring-driven pre-dispensing movement before the corresponding dose is dispensed, as the selection of the dose requires transition of the drive member from one of those two teeth into the subsequent tooth. If the distance between two teeth is greater than or equal to a minimum distance the drive member has to be moved for pre-loading spring member 18, a spring-driven pre-dispensing movement of the drive member and the piston rod takes place. In particular, the distance between the first, most distal tooth of the piston rod 13 from the subsequent tooth may be greater than the distance between subsequent pairs of adjacent teeth, preferably greater than the distance between all of the subsequent pairs of adjacent teeth. Accordingly, a pre-dispensing movement of the drive member may only occur before delivering the first dose of fluid. Thus, the piston rod may be configured to restrict the pre-dispensing or priming movement of the piston rod 13 to certain actuations of the drive member 5 by adjusting the distance between the teeth 14a accordingly.

FIG. 5 shows the result after a partial relief of pre-dispensing member 18. The force generated by pre-dispensing member 18 causes a drive member 5 to move by a pre-dispensing distance towards the distal end of drug delivery device 1. Due to such pre-dispensing movement, displacement member 17 comes in direct contact with tooth portion 14 of teeth 14a of piston rod 13. Accordingly, the drive member 5 also exerts a force caused by pre-dispensing member 18 upon piston rod 13 which may cause piston rod 13 to move also towards the distal end if possible. Any pre-dispensing distance movement will be stopped or at least slowed down if piston rod 13 comes in direct contact with the piston arranged in the cartridge of the drug delivery device.

As a result, all mechanical parts including drive member 5, a piston rod 13 and the piston will be in direct contact and no tolerances or backlashes will remain. A user, pushing the button for dispensing a fluid will now exert a force towards the distal end of drug delivery device 1 resulting in a distal movement 20 of drive member 5. Each distal movement of drive member 5 is directly and without any delay transferred to piston rod 13 by displacement member 17. The bung is pushed forward and the correct amount of fluid dispensed.

FIG. 7 shows another embodiment of the present invention. In this embodiment, the drive member comprises a first fixed rack 2a which is operatively connected to a moving rack 5a. The fixed rack 2a comprises a stop element 15 on which a portion of moving element 5a is sliding. Moving element 5a also comprises two stop elements 16, which surround element 15 such that the stop element 15 of fixed rack 2a is arranged in between. Accordingly, moving rack 5*a* can be moved along distal and proximal direction only between the two stop elements 16.

While the fixed rack 2 is attached firmly to the housing, moving rack 5*a* can move along distal and proximal direction within the housing and is operatively connected to the piston rod (not shown). Moving rack 5*a* further comprises a pre-dispensing spring member 18 having a first strip portion 28 and a second strip portion 29. Both portions are connected together in a v-like shape. Second portion 29 is also arranged between one of the stop elements 16 and the stop element 15 of fixed rack 2*a*. By moving the rack 5*a* towards proximal end 12, second strip portion 29 of spring element 18 comes in contact with stop element 15 of fixed rack 2*a*. The second strip portion is now stressed due to the bended arrangement of the spring member 18. This stress will in turn result in a smaller force towards the distal end. After release, the moving rack 5*a* will move by a pre-dispensing distance towards distal end 11. This pre-dispensing distance will compensate for any tolerance or backlashes between the different mechanical parts and particularly between the moving rack 5*a* and piston rod 13.

Figure 6:
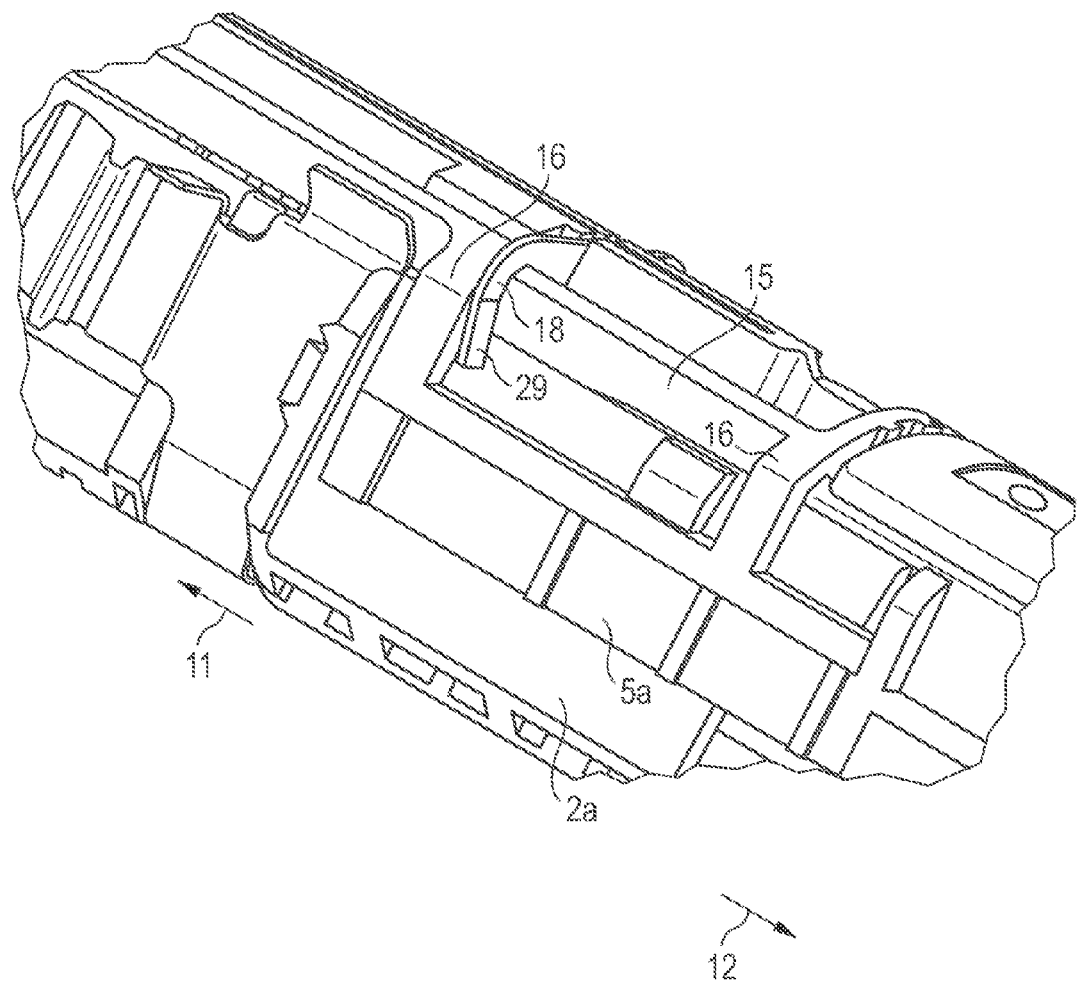
FIG. 6 illustrates another embodiment of the present invention.

FIG. 7 shows an embodiment of a drug delivery device with a drive member as indicated in FIG. 6. The drug delivery device comprises piston rod stop member 22 preventing the piston rod 13 from being moved towards proximal end 12. The moving rack comprises an opening in which stop element 15 of fixed rack 2*a* is protected. By moving the moving rack 5*a* along proximal direction, stop element 16 of moving rack 5*a* comes in contact with spring element 18 arranged on one of the sides of stop element 15. Spring element 18 will exert a force directed towards the distal end to achieve a movement by a pre-dispensing distance of moving rack 5*a* as well as piston rod 13, which is in operative connection with moving rack 5*a*.

Still, a force generated by spring element 18 may not be strong enough to overcome the adhesion force between the bung and the cartridge or the bung and the housing. Accordingly, the movement by a pre-dispensing distance will not dispense any fluid.

The additional spring element generates a force after a dose is selected and before dispensing the selected dose, which compensates for any tolerances and backlashes occurring between different dispense shots. As a result, accuracy of the selection will increase as any backlashes or tolerances in the mechanical part of the drug delivery device are compensated.

The invention claimed is:

1. A drug delivery device, comprising:
a housing;
a piston rod arranged in the housing and adapted to be moved along an axial direction to dispense a fluid;
a drive member arranged in the housing, operatively coupled to the piston rod and adapted to set a dose of fluid for dispensing in response to a first movement of the drive member in a proximal direction and to move the piston rod along the axial direction to dispense the dose in response to a second movement of the drive member in a distal direction;
a pre-dispensing spring member operatively coupled to the drive member and the housing and adapted to move at least the drive member by a pre-dispensing distance axially in a distal direction between the first and second movement thereby compensating for any tolerance or backlashes between the piston rod and the drive member.

2. The drug delivery device according to claim 1, wherein the pre-dispensing spring member comprises a first strip portion and a second strip portion connected slightly bent to the first strip portion.

3. The drug delivery device according to claim 1, wherein the pre-dispensing spring member comprises a bended strip.

4. The drug delivery device according to claim 1, wherein the pre-dispensing spring member comprises a torsional stress at least after the first movement of the drive member.

5. The drug delivery device according to claim 1, wherein the pre-dispensing spring member is adapted to exert a force upon the drive member after the first movement, said force at least partly directed towards the direction of the second movement.

6. The drug delivery device according to claim 1, wherein the housing comprises a stop element adapted to stop a motion of the drive member in the direction of the first movement, wherein the pre-dispensing spring member is attached to the stop element.

7. The drug delivery device according to claim 1, wherein the housing comprises a stop element adapted to stop a motion of the drive member in the direction of the first movement, wherein the pre-dispensing spring member is attached to the drive member.

8. The drug delivery device according to claim 1, further comprising
a dose button, operatively connected to the drive member and adapted to excite the first movement of the drive member in response to a first movement of the button and adapted to excite the second movement of the drive member in response to a second movement of the button.

9. The drug delivery device according to claim 8, wherein the pre-dispensing spring member is attached to the housing and the dose button to exert a force upon the dose button in response to the first movement of the dose button, said force at least partly directed in the direction of the second movement of the dose button.

10. The drug delivery device according to claim 8 or any claim depending thereon, wherein the dose button is adapted to be moved in axial distal direction to set the dose of fluid.

11. The drug delivery device according to claim 8, wherein the dose button is adapted to be rotated to set the dose of fluid.

12. The drug delivery device according to claim 1, wherein the pre-dispensing spring element is tensioned during the first movement and relaxes at least partly before the second movement, thereby driving at least the drive member the pre-dispensing distance.

13. The drug delivery device according to claim 1, further comprising:
a cartridge having the fluid;
a piston movably arranged in the cartridge, wherein the piston rod is adapted to drive the piston.

14. The drug delivery device according to claim 13, wherein an adhesion force between the piston and the cartridge holder or between the piston and the housing is greater than a force which is exerted by the pre-dispensing spring member during the first and second movement and transferred to the piston.

15. The drug delivery device according to claim 1, wherein the pre-dispensing spring member comprises a lift in the range of less than 10%, preferably less than 5% of a movement distance during dispense of the fluid or the second movement.

16. A drug delivery device, comprising:
- a housing;
- a piston rod arranged in the housing and adapted to be moved along an axial direction to dispense a fluid by moving a piston in a cartridge;
- a drive member arranged in the housing, operatively coupled to the piston rod and adapted to set a dose of fluid for dispensing in response to a first movement of the drive member in a proximal direction and to move the piston rod along the axial direction to dispense the dose in response to a second movement of the drive member in a distal direction;
- a pre-dispensing spring member operatively coupled to the drive member and the housing and adapted to move at least the drive member by a pre-dispensing distance axially in a distal direction between the first and second movement thereby compensating for any tolerance or backlashes between different parts of the drive member as well as any tolerances between the piston and the piston rod or the piston rod and the drive member.

* * * * *